United States Patent
Yamamoto et al.

(10) Patent No.: US 8,815,065 B2
(45) Date of Patent: Aug. 26, 2014

(54) ELECTROCHEMICAL GAS SENSOR AND MOUNTING STRUCTURE THEREFOR

(71) Applicant: Figaro Engineering Inc., Mino (JP)

(72) Inventors: Yoshihiro Yamamoto, Mino (JP); Masafumi Okada, Mino (JP); Kuniyuki Izawa, Mino (JP); Tomoyasu Honda, Mino (JP)

(73) Assignee: Figaro Engineering Inc., Osaka (JP)

(*) Notice: Subject to any disclaimer, the term of this patent is extended or adjusted under 35 U.S.C. 154(b) by 34 days.

(21) Appl. No.: 13/763,747

(22) Filed: Feb. 11, 2013

(65) Prior Publication Data

US 2014/0083852 A1    Mar. 27, 2014

(30) Foreign Application Priority Data

Sep. 25, 2012  (JP) .................................. 2012-210391

(51) Int. Cl.
*G01N 27/407*    (2006.01)

(52) U.S. Cl.
CPC ........ *G01N 27/4073* (2013.01); *G01N 27/4074* (2013.01); *G01N 27/4072* (2013.01)
USPC ........................... 204/415; 204/431; 73/23.31

(58) Field of Classification Search
USPC .................................. 204/400–429; 73/23.31
See application file for complete search history.

(56) References Cited

U.S. PATENT DOCUMENTS

| 5,897,766 | A | * | 4/1999 | Kawatsu | 204/426 |
| 6,896,781 | B1 |  | 5/2005 | Shen et al. |  |
| 7,381,314 | B2 |  | 6/2008 | Inoue et al. |  |
| 7,393,505 | B2 |  | 7/2008 | Inoue et al. |  |
| 2004/0134780 | A1 | * | 7/2004 | Inoue et al. | 204/424 |
| 2008/0145722 | A1 | * | 6/2008 | Coignet et al. | 429/13 |
| 2011/0048943 | A1 | * | 3/2011 | Nemes | 204/415 |

FOREIGN PATENT DOCUMENTS

WO        2011/096106 A1    8/2011

OTHER PUBLICATIONS

EP 2711700 containing search report published Mar. 26, 2014.*

* cited by examiner

*Primary Examiner* — Jennifer Dieterle
(74) *Attorney, Agent, or Firm* — Keating & Bennett, LLP

(57) ABSTRACT

A sensor body of an electrochemical gas sensor having no water reservoir is housed in a metal can including a sensing electrode on one surface of a proton-conducting membrane or a separator retaining an electrolyte and a counter electrode on the opposite surface thereof. The counter electrode is supported by and electrically connected to the metal can via a connecting member. The sensing electrode is connected to a diffusion control plate with the sensing electrode-side ring member, and the ring member is conductive and includes a hole at a center thereof that is connected to a hole of the diffusion control plate.

8 Claims, 4 Drawing Sheets

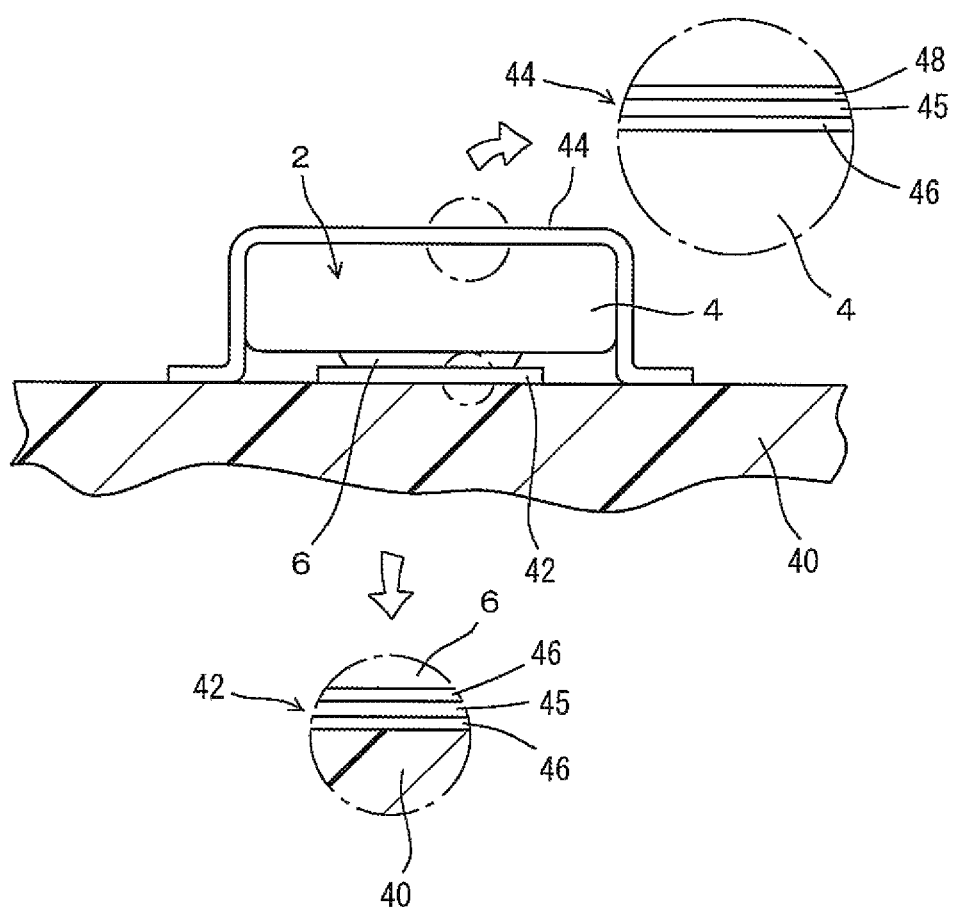
F I G. 7

ELECTROCHEMICAL GAS SENSOR AND MOUNTING STRUCTURE THEREFOR

BACKGROUND OF THE INVENTION

1. Field of the Invention

The present invention relates to an electrochemical gas sensor and a mounting structure therefor.

2. Description of the Related Art

In a proton-conductive gas sensor, water vapor is supplied from a water reservoir to a proton-conducting membrane. For example, according to U.S. Pat. No. 6,896,781, a proton-conducting membrane is provided with a sensing electrode on one surface and a counter electrode on the opposite surface, and each of the sensing electrode and the counter electrode is covered with a hydrophilic conductive membrane, which is hydrophobic, gas-permeable, and conductive. Here, an assembly of a proton-conducting membrane, a sensing electrode and a counter electrode is called an "MEA" (membrane electrode assembly). According to U.S. Pat. No. 6,896,781, a water reservoir is provided on the counter electrode side and an atmosphere to be detected is supplied from the sensing electrode side, thus preventing water in the water reservoir from overflowing to the proton-conducting membrane due to the presence of the hydrophilic conductive membrane.

The Applicant of the present application has proposed to provide a gas sensor using a proton conductor with a metal plate having a diffusion control hole formed therein on the sensing electrode side of the gas sensor, thus controlling gas diffusion to the sensing electrode (see, for example, U.S. Pat. No. 7,393,505). The Applicant of the present application has also proposed that a separator, instead of a proton conductor, may retain an electrolyte (see, for example, U.S. Pat. No. 7,381,314). Moreover, the Applicant of the present application has proposed omitting the water reservoir, measuring the impedance of the proton-conducting membrane or the separator, and correcting a reduction in output of the gas sensor in a dry atmosphere by the impedance of the proton-conducting membrane or the like (see, for example, WO 2011/96106A). As a result of investigating how to increase the gas sensitivity of an electrochemical gas sensor having no water reservoir, the present inventors have developed and achieved the preferred embodiments of the present invention.

SUMMARY OF THE INVENTION

A preferred embodiment of the present invention increases the gas sensitivity of an electrochemical gas sensor having no water reservoir.

Another preferred embodiment of the present invention facilitates and simplifies mounting of an electrochemical gas sensor having no water reservoir onto a circuit board.

An electrochemical gas sensor having no water reservoir according to a preferred embodiment of the present invention includes a sensor body including a sensing electrode on one surface of a proton-conducting membrane or a separator retaining an electrolyte, and a counter electrode on an opposite surface thereof; a metal can housing the sensor body and including a bottom inner surface opposing the counter electrode; a connecting member disposed between the metal can and the counter electrode so as to support the counter electrode by the metal can and electrically connect the metal can and the counter electrode to each other; a diffusion control plate made of metal, the diffusion control plate opposing the sensing electrode and including a diffusion control hole; and a sensing electrode-side ring member disposed between the sensing electrode and the diffusion control plate, the sensing electrode-side ring member being a conductive ring member including a hole at a center thereof, connected to the diffusion control hole and including a larger diameter than the diffusion control hole. The bottom inner surface is a surface located at the bottom of the metal can and also inside the can, assuming that the metal can is a container. This surface opposes the counter electrode. In addition, the diffusion control hole faces the hole of the ring member.

Since the electrochemical gas sensor has no water reservoir, the sensing electrode-side ring member including a hole at its center may be used. The use of the sensing electrode-side ring member including a hole at its center increases the gas sensitivity as shown in FIGS. 5 and 6. Furthermore, the sensing electrode-side ring member electrically connects the sensing electrode and the diffusion control plate to each other.

Preferably, the connecting member includes a counter electrode-side ring member, which is a conductive ring including a hole at its center. This allows the counter electrode to be supported by the metal can with the counter electrode-side ring member.

Also preferably, the sensing electrode-side ring member includes a gas-permeable ring member that is preferably formed by binding carbon powder with a binder. The gas-permeable ring member to which carbon powder are bound with the binder electrically connects the sensing electrode and the diffusion control plate to each other, and will not corrode even if an acidic substance such as a proton conductor is present therearound.

Preferably, the sensing electrode-side ring member is provided with a conductive adhesive layer or a conductive sticky layer on one surface of the conductive substrate and coupled to the diffusion control plate both electrically and physically with the adhesive layer or the sticky layer. The sensing electrode-side ring member is provided with a conductive adhesive layer or a conductive sticky layer on the opposite surface of the conductive substrate and coupled to the sensing electrode in the same manner. This allows the sensing electrode to be easily fixed to the diffusion control plate via the ring member, and also allows the sensing electrode and the diffusion control plate to be electrically connected to each other.

Preferably, the counter electrode-side ring member includes a conductive substrate and conductive adhesive layers or conductive sticky layers provided on both surfaces thereof, the counter electrode-side ring member is coupled to a bottom inner surface of the metal can with the conductive adhesive layer or the conductive sticky layer on one of the surfaces of the conductive substrate, and the counter electrode-side ring member is coupled to the counter electrode with the conductive adhesive layer or the conductive sticky layer on the opposite surface of the conductive substrate. This allows the counter electrode to be easily fixed to the metal can via the counter electrode-side ring member, and also allows the counter electrode and the metal can to be electrically connected to each other.

Preferably, there is provided a seal including a metal container housing a filter material so as to be in contact with a surface of the diffusion control plate opposite to the sensing electrode. The seal is provided with a hole connected to the diffusion control hole and a hole disposed on a side opposite to the diffusion control plate so as to introduce an atmosphere to be detected, and the seal is fixed to an opening of the metal can via a gasket. The seal serves as a terminal on the sensing electrode side, the metal can serves as a terminal on the counter electrode side, and the gasket is insulating. In the seal, the atmosphere to be detected is introduced from the hole on the side opposite to the diffusion control plate, is removed of any unnecessary component with the filter material, and thereafter introduced to the diffusion control hole.

Another preferred embodiment of the present invention provides a mounting structure arranged to fix an electrochemical gas sensor onto a circuit board, the electrochemical gas sensor including a sensor body including a sensing electrode on one surface of a proton-conducting membrane or a separator retaining an electrolyte, and a counter electrode on an opposite surface thereof, a metal can housing the sensor body and including a bottom inner surface opposing the counter electrode; a connecting member disposed between the metal can and the counter electrode so as to support the counter electrode by the metal can and electrically connect the metal can and the counter electrode to each other; a diffusion control plate made of metal, the diffusion control plate opposing the sensing electrode and including a diffusion control hole; a sensing electrode-side ring member disposed between the sensing electrode and the diffusion control plate, the sensing electrode-side ring member being a conductive ring member including a hole at the center of its ring, the hole being connected to the diffusion control hole and including a larger diameter than the diffusion control hole; and a seal including a metal container housing a filter material so as to be in contact with a surface of the diffusion control plate opposite to the sensing electrode, the seal including a hole connected to the diffusion control hole and a hole disposed on a side opposite to the diffusion control plate so as to introduce an atmosphere to be detected, and the seal being fixed to an opening of the metal can via a gasket, the electrochemical gas sensor having no water reservoir, a surface of the seal on a side opposite to the diffusion control plate being fixed and electrically connected to the circuit board with a conductive adhesive tape.

Preferably, the mounting structure also includes another conductive adhesive tape electrically connecting a bottom surface of the metal can on a side opposite to the sensor body to the circuit board. The present mounting structure allows the electrochemical gas sensor to be easily mounted and electrically connected onto the circuit board. In particular, the two conductive adhesive tapes make electrical connections between the sensing electrode and the circuit board and also between the counter electrode and the circuit board.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 7 is a diagram showing a structure arranged to mount the electrochemical gas sensor according to a preferred embodiment of the present invention to a printed board.

DETAILED DESCRIPTION OF THE PREFERRED EMBODIMENTS

Figure 1:
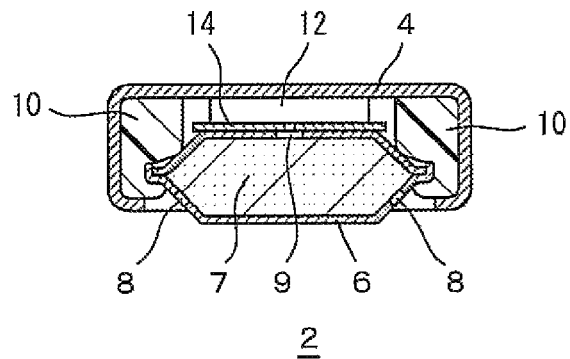
FIG. 1 is a cross-sectional view of an electrochemical gas sensor according to a preferred embodiment of the present invention.

The following describes various preferred embodiments of the present invention.

FIGS. 1 to 7 show an electrochemical gas sensor 2 according to preferred embodiments of the present invention and modifications thereof. In the drawings, reference numeral 4 denotes a metal can. Reference numeral 6 denotes a seal, which is a container that is preferably formed, for example, by welding or crimping two metal plates placed upon each other at their periphery, and housing a filter material 7 therein. The seal 6 includes openings 8 on the atmosphere to be detected side and an opening 9 on the diffusion control plate 14 side, and thus seals the opening of the metal can 4. The material of the metal can 4 and the seal 6 may preferably be, for example, stainless steel, nickel or the like. The filter material 7 may preferably be, for example, activated carbon, activated clay, zeolite, silica gel, or the like, and removes any unnecessary gas by adsorption. Reference numeral 10 denotes a gasket preferably made of a synthetic resin or other suitable material. The gasket 10 is insulating and hermetically seals the gap between the seal 6 and the metal can 4. Reference numeral 12 denotes a sensor portion, which preferably includes a sensor body 16 and a sensing electrode-side ring member 22 and a counter electrode-side ring member 24 disposed on both surfaces thereof. Reference numeral 14 denotes a diffusion control plate, which preferably is a metal thin plate. The diffusion control plate 14 includes a diffusion control hole 15 with a diameter of about 0.1 mm, for example, located at its center or approximately at its center. The diffusion control hole 15 is connected to the opening 9 of the seal 6, and the opening 9 has a large diameter. The bottom, top, and so forth of the metal can 4 indicate directions when the metal can 4 is viewed from below in FIG. 1.

The sensor body 16 preferably includes a proton-conducting membrane 20, a sensing electrode 18 provided on one surface thereof, and a counter electrode 19 provided on the opposite surface of the proton-conducting membrane 20. The proton-conducting membrane 20 may be changed to a different solid electrolyte membrane such as a hydroxide ion conductor, for example. Alternatively, the proton-conducting membrane 20 may be changed to a separator in which an electrolyte is supported on a porous synthetic resin sheet, for example. Here, the term "separator" is used in the sense of separating the electrodes 18 and 19. A bottom inner surface 21 of the metal can 4 opposes the counter electrode 19, and the sensing electrode 18 opposes the diffusion control plate 14.

Figure 2:
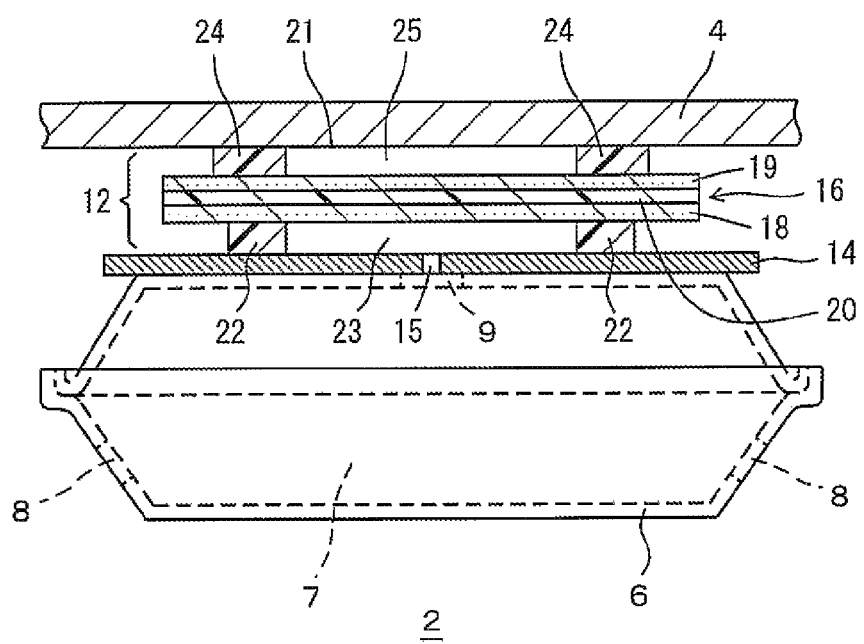
FIG. 2 is a cross-sectional view of a relevant portion of FIG. 1.

The ring members 22 and 24 are preferably formed by binding carbon powder with a binder such as tetrafluoroethylene, and are hydrophobic, conductive, and gas-permeable, for example. The ring members 22 and 24 are preferably ring-shaped in plan view, for example. The ring member 22 includes a large diameter hole 23 at its center or approximately at its center, and the ring member 24 has a large diameter hole 25 at its center or approximately at its center. Assuming that the diameter of the sensor body 16 is, for example, about 10 mm, the diameter of the ring members 22 and 24 preferably is, for example, about 5 mm to about 10 mm. The diameter of the holes 23 and 25 preferably is, for example, about 0.5 mm to about 5 mm, is smaller than the diameter of the ring members 22 and 24, and is preferably about 2 mm to about 4 mm, for example. The thickness of the ring members 22 and 24 preferably is, for example, about 0.1 mm to about 0.5 mm, and more preferably about 0.2 mm to about 0.4 mm, for example. Also, the hole 23 of the ring member 22 on the sensing electrode 18 side is configured to distribute the atmosphere to be detected from the diffusion control hole 15 to the sensing electrode 18. The hole 25 of the ring member 24 on the counter electrode 19 side is configured to store air and supply oxygen to the counter electrode 19. The ring member 22 electrically connects the sensing electrode 18 to the seal 6, and fixes the sensing electrode 18 to the seal 6 using the pressure applied from the gasket 10. Meanwhile, the ring member 24 electrically connects the counter electrode 19 to the metal can 4, and fixes the counter electrode 19 to the metal can 4. In FIG. 2, the ring member 22 is shown as preferably having a smaller diameter than the ring member 24. However, the ring member 22 may have the same diameter as the ring member 24, or may have a larger diameter than the ring member 24. Furthermore, the holes 23 and 25 may have the same diameter, or may have different diameters. In particular, the hole 25 on the counter electrode 19 side need not be provided. In addition, the holes 23 and 25 need not be concentric with the ring members 22 and 24.

Figure 3:
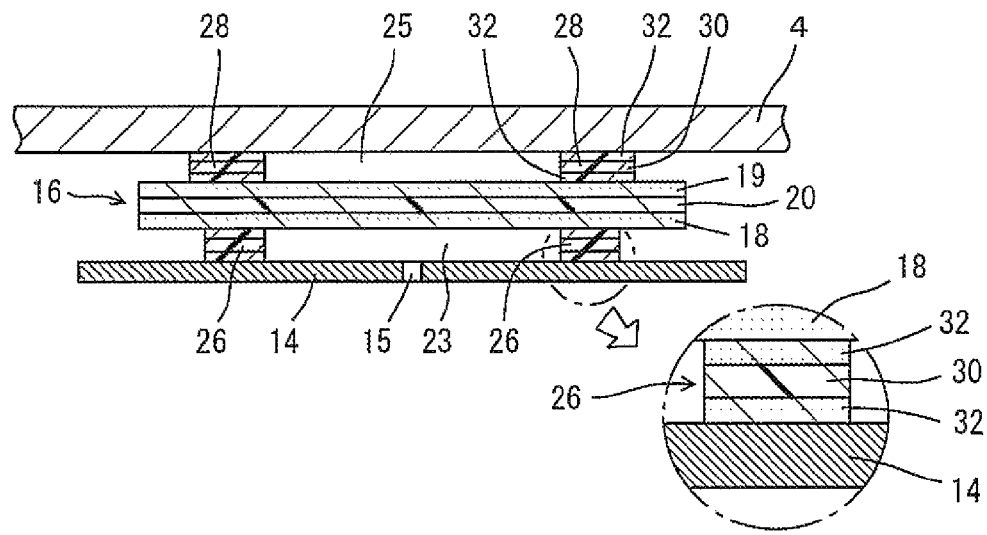
FIG. 3 is an enlarged cross-sectional view of a relevant portion of an electrochemical gas sensor according to a modification.

FIG. 3 shows an electrochemical gas sensor according to a modification of a preferred embodiment of the present invention, which is the same as the gas sensor 2 according to the preferred embodiment shown in FIGS. 1 and 2 except for the following points. Reference numeral 26 denotes a sensing electrode-side ring member, and reference numeral 28 denotes a counter electrode-side ring member. The shape, size, and so forth of the ring members 26 and 28 are preferably the same or substantially the same as their counterparts in the preferred embodiment shown in FIGS. 1 and 2. The ring members 26 and 28 each preferably include a conductive substrate 30 and conductive adhesive layers 32 disposed on both surfaces thereof. The conductive substrate 30 is, for example, a substrate of synthetic resin fiber that has been made conductive by being electrolessly plated with Ni, Cu or the like, and is provided with a carbon coating layer (not shown) made of, for example, a mixture of a carbon black and a binder. Note that the carbon coating layer may be configured in any manner. The proton-conducting membrane 20 preferably is an acidic substance, and the occurrence of condensation in the sensor portion 12 may result in low pH water, which may lead to corrosion of the plating layer of Ni or the like. Therefore, the carbon coating layer is used to prevent water from reaching the plating layer of Ni or the like. Note that the carbon coating layer need not be provided. For example, the need for the carbon coating layer may be eliminated by reducing the acidity of the proton-conducting membrane 20 or using a hydroxide ion conducting-membrane or the like.

The conductive adhesive layer 32 preferably is made of, for example, a mixture of an epoxy resin and a conductive filler such as carbon. Alternatively, a conductive sticky layer made of a mixture of an acrylic resin or the like and a conductive filler may be used, for example. The ring members 26 and 28 according to the modification of a preferred embodiment of the present invention shown in FIG. 3 are hermetically sealed, fix and electrically connect the sensing electrode 18 to the diffusion control plate 14, and fix and electrically connect the counter electrode 19 to the inner surface 21 of the metal can 4.

Figure 4:
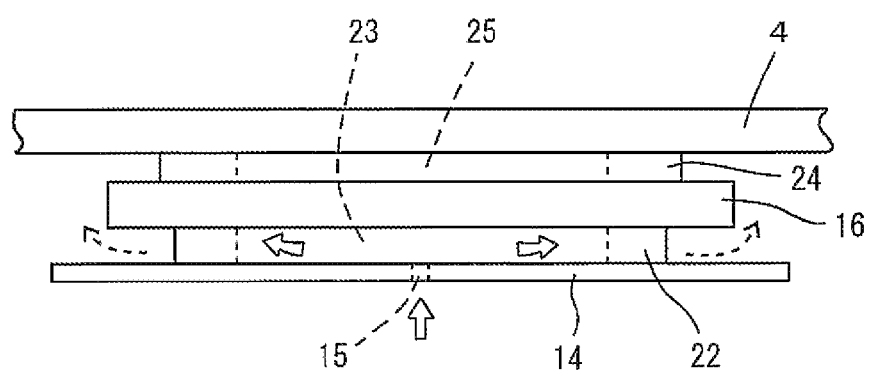
FIG. 4 is a diagram schematically showing a gas flow in the gas sensor according to a preferred embodiment of the present invention.

FIG. 4 shows a diffusion model of the atmosphere to be detected in the electrochemical gas sensor 2. The atmosphere passes through the diffusion control hole 15 to reach the hole 23 at the center of the ring member 22, thus diffusing to the sensing electrode 18. According to a conventional example without a hole 23, there is the possibility that a carbon sheet may form a diffusion resistance, and also that the diffusion resistance of the carbon sheet may provide bypasses for the atmosphere to the counter electrode 19 side as indicated by the dashed lines in FIG. 4. Note that the carbon sheet mentioned here corresponds to the ring members 22 and 24 without the holes 23 and 25. In contrast, according to the present preferred embodiment of the present invention, the atmosphere is supplied from the hole 23 to the sensing electrode 18, and the amount of the atmosphere supplied is controlled only with the diffusion control hole 15. Furthermore, the hole 25 is configured to store air, and supply oxygen to the counter electrode 19.

Figure 5:
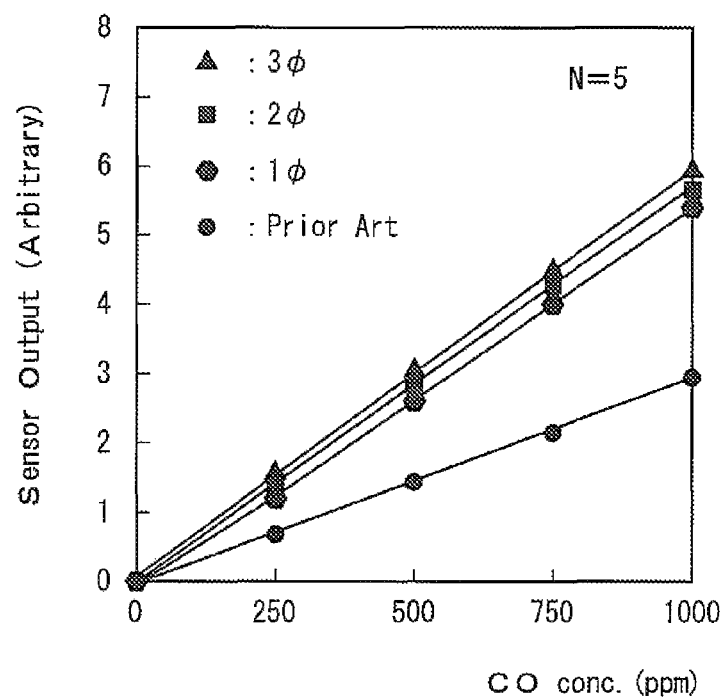
FIG. 5 is a characteristic diagram illustrating the relationship between the hole diameter of a sensing electrode-side ring member and the gas sensitivity.
Figure 6:
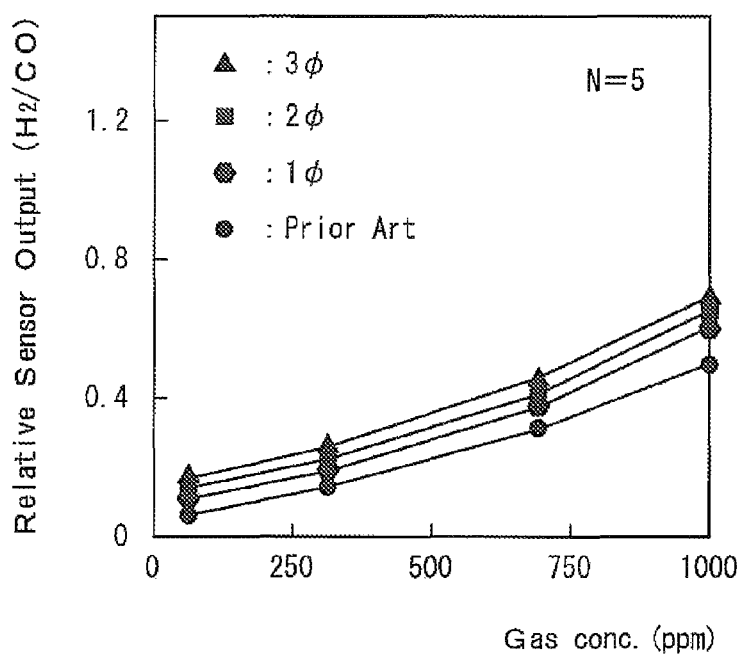
FIG. 6 is a characteristic diagram illustrating the relationship between the hole diameter of the sensing electrode-side ring member and the relative sensitivity between hydrogen and CO.

FIGS. 5 and 6 show the characteristics of the electrochemical gas sensor 2 according to a preferred embodiment of the present invention, with the diameter of the holes 23 and 25 varied to be 0 (the conventional example), about 1 mm, about 2 mm, and about 3 mm, for example. Furthermore, the thickness of the ring members 22 and 24 preferably is about 0.3 mm, and the results are shown by the average of five sensors. As shown in FIG. 5, the provision of the holes 23 and 25 increased the CO sensitivity. Note that the presence or absence of the hole 25 does not affect the gas sensitivity, and the provision of the hole 23 increased the gas sensitivity and the gas sensitivity gradually increased as the diameter of the hole 23 was increased.

FIG. 6 shows the sensor output to hydrogen taking the sensor output to CO having the same concentration as 1 (the relative sensitivity to hydrogen). The provision of the hole 23 increased the relative sensitivity to hydrogen, but not to such an extent that the CO detection was prevented. An increased CO sensitivity and an increased relative sensitivity to hydrogen indicate either that the hole 23 facilitates the diffusion of the atmosphere to be detected from the diffusion control hole 15 to the sensing electrode 18; or that the hole 23 inhibits the entry of the atmosphere to be detected to the counter electrode 19.

FIG. 7 shows a structure arranged to mount the electrochemical gas sensor 2 onto a printed board 40, and the electrochemical gas sensor according to the modification described above with respect to FIG. 3 may also be mounted in the same manner. Reference numerals 42 and 44 denote adhesive tape. The adhesive tape 42 is preferably formed by providing conductive adhesive layers 46 on both surfaces of a metal film 45 of Cu, Ni or other suitable material, for example. The conductive adhesive layers 46 may be replaced by conductive sticky layers, for example. The adhesive tape 44 is preferably formed by providing a conductive adhesive layer 46 on a surface of the metal film 45 of Cu, Ni or other suitable material on the metal can 4 side, and an insulating film 48 on the opposite surface thereof. The conductive adhesive layer 46 may be a conductive sticky layer, for example. The insulating film 48 need not be provided. The adhesive tape 42 serves to fix the surface of the seal 6 on the side opposite to the diffusion control plate (the surface on the atmosphere to be detected side) to the wiring (not shown) of the printed board 40. Meanwhile, the adhesive tape 44 extends from the top (the bottom surface when viewed from the seal 6 side) of the metal can 4, for example, along the side surface thereof, thus fixing the top of the metal can 4 to the wiring (not shown) of the printed board 40. Accordingly, as compared to when the gas sensor 2 is fixed to a dedicated holder (not shown), the electrochemical gas sensor 2 can be easily mounted onto the printed board 40. The adhesive tape 44 may be only an electrical connection between the top surface of the metal can 4 and the printed board 40. Specifically, the tape 44 connects the top surface and a printed circuit on the board 40. The tape 44 may not extend along the side of the metal can 4 and may extend only along one side of the metal can 4.

Since the electrochemical gas sensor 2 has no water reservoir, a reduction in the relative humidity causes an increase in the impedance of the proton-conducting membrane 20, which in turn reduces the sensitivity to a gas such as CO. Therefore, in the manner as described in WO2011/96106A, for example, the impedance of the proton-conducting membrane 20 is measured and the influence of the relative humidity is corrected. The gas to be detected may be any gas, such as CO, hydrogen, ethanol, or ammonia, for example.

Accordingly, a preferred embodiment of the present invention preferably includes the following features:
1) No water reservoir is provided.
2) Since no water reservoir is provided, the ring members 22 to 28 may be used in place of a hydrophobic conducting membrane.
3) The hole 23 of the ring members 22 and 26 increases the gas sensitivity.
4) The use of the ring members 26 and 28 including the adhesive layers 32 on both surfaces allows the sensor body 16 to be easily fixed to the metal can 4 and the diffusion control plate 14.
5) The mounting structure shown in FIG. 7 allows the gas sensor 2 to be easily mounted onto the printed board 40.

The following is a non-limiting example of a description of the reference numerals described above and shown in the drawings:
2 Electrochemical gas sensor
4 Metal can
6 Seal
7 Filter material
8, 9 Opening
10 Gasket
12 Sensor portion
14 Diffusion control plate
15 Diffusion control hole
16 Sensor body
18 Sensing electrode
19 Counter electrode
20 Proton-conducting membrane
21 Bottom inner surface
22, 26 Sensing electrode-side ring member
24, 28 Counter electrode-side ring member
23, 25 Hole
30 Conductive substrate
32 Conductive adhesive layer
40 Printed board
42, 44 Adhesive tape
45 Metal film
46 Conductive adhesive layer
48 Insulating film While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. An electrochemical gas sensor having no water reservoir, the electrochemical gas sensor comprising:
a sensor body including a sensing electrode on one surface of a proton-conducting membrane or a separator retaining an electrolyte, and a counter electrode on an opposite surface thereof;
a metal can housing the sensor body and including a bottom inner surface opposing the counter electrode;
a connecting member disposed between the metal can and the counter electrode so as to support the counter electrode by the metal can and electrically connect the metal can and the counter electrode to each other;
a diffusion control plate made of metal, the diffusion control plate opposing the sensing electrode and including a diffusion control hole; and
a sensing electrode-side ring member disposed between the sensing electrode and the diffusion control plate, the sensing electrode-side ring member being a conductive ring member including a hole at a center or approximately at a center thereof, connected to the diffusion control hole and having a larger diameter than the diffusion control hole.

2. The electrochemical gas sensor according to claim 1, wherein the connecting member includes a counter electrode-side ring member, which is a conductive ring including a hole at a center or approximately at a center thereof.

3. The electrochemical gas sensor according to claim 1, wherein the sensing electrode-side ring member includes a gas-permeable ring member including carbon powder that has been bound with a binder.

4. The electrochemical gas sensor according to claim 1, wherein the sensing electrode-side ring member is provided with a conductive adhesive layer or a conductive sticky layer on one surface of a conductive substrate and coupled to the diffusion control plate, and is provided with a conductive adhesive layer or a conductive sticky layer on an opposite surface of the conductive substrate and coupled to the sensing electrode.

5. The electrochemical gas sensor according to claim 4, wherein
the counter electrode-side ring member includes a conductive substrate and conductive adhesive layers or conductive sticky layers provided on both surfaces thereof;
the counter electrode-side ring member is coupled to a bottom inner surface of the metal can with the conductive adhesive layer or the conductive sticky layer on one of the surfaces of the conductive substrate; and
the counter electrode-side ring member is coupled to the counter electrode with the conductive adhesive layer or the conductive sticky layer on the opposite surface of the conductive substrate.

6. The electrochemical gas sensor according to claim 1, further comprising a seal including a metal container housing a filter material so as to be in contact with a surface of the diffusion control plate opposite to the sensing electrode, wherein the seal is provided with a hole connected to the diffusion control hole and a hole disposed on a side opposite to the diffusion control plate so as to introduce an atmosphere to be detected, and the seal is fixed to an opening of the metal can via a gasket.

7. A mounting structure arranged to fix an electrochemical gas sensor onto a circuit board, the electrochemical gas sensor comprising:
a sensor body including a sensing electrode on one surface of a proton-conducting membrane or a separator retaining an electrolyte, and a counter electrode on an opposite surface thereof,
a metal can housing the sensor body and including a bottom inner surface opposing the counter electrode;
a connecting member disposed between the metal can and the counter electrode so as to support the counter electrode by the metal can and electrically connect the metal can and the counter electrode to each other;

a diffusion control plate made of metal, the diffusion control plate opposing the sensing electrode and including a diffusion control hole;

a sensing electrode-side ring member disposed between the sensing electrode and the diffusion control plate, the sensing electrode-side ring member being a conductive ring member including a hole at a center or approximately at a center thereof, connected to the diffusion control hole and including a larger diameter than the diffusion control hole; and a seal including a metal container housing a filter material so as to be in contact with a surface of the diffusion control plate opposite to the sensing electrode; wherein the seal includes a hole connected to the diffusion control hole and a hole disposed on a side opposite to the diffusion control plate so as to introduce an atmosphere to be detected;

the seal is fixed to an opening of the metal can via a gasket;

the electrochemical gas sensor has no water reservoir; and a surface of the seal on a side opposite to the diffusion control plate is fixed and electrically connected to the circuit board with a conductive adhesive tape.

8. The mounting structure according to claim 7, wherein the mounting structure further comprises another conductive adhesive tape electrically connecting a bottom surface of the metal can on a side opposite to the sensor body to the circuit board.

\* \* \* \* \*